(12) United States Patent
Babin et al.

(10) Patent No.: US 7,052,887 B2
(45) Date of Patent: May 30, 2006

(54) METHOD FOR IMMOBILIZATION OF (AN) AFFINITY REAGENT(S) ON A HYDROPHOBIC SOLID PHASE

(75) Inventors: Fabienne Babin, Montigny le Bretonneux (FR); Laurence Hamon, Paris (FR); François Rieunier, Bois d'Arcy (FR)

(73) Assignee: Bio-Rad Pasteur, Marnes la Coquette (FR)

( * ) Notice: Subject to any disclaimer, the term of this patent is extended or adjusted under 35 U.S.C. 154(b) by 427 days.

(21) Appl. No.: 10/181,090

(22) PCT Filed: Jan. 12, 2001

(86) PCT No.: PCT/FR01/00095

§ 371 (c)(1),
(2), (4) Date: Nov. 12, 2002

(87) PCT Pub. No.: WO01/51927

PCT Pub. Date: Jul. 19, 2001

(65) Prior Publication Data

US 2004/0052797 A1 Mar. 18, 2004

(30) Foreign Application Priority Data

Jan. 13, 2000 (FR) .................................. 00 00376

(51) Int. Cl.
C12N 11/00 (2006.01)
C12N 11/14 (2006.01)
C12N 11/08 (2006.01)
C12N 11/06 (2006.01)

(52) U.S. Cl. ...................... 435/174; 435/176; 435/180; 435/181

(58) Field of Classification Search ................ 435/174, 435/175, 176, 178, 179, 180, 181
See application file for complete search history.

(56) References Cited

U.S. PATENT DOCUMENTS

| 4,486,539 A | 12/1984 | Ranki et al. |
| 4,563,419 A | 1/1986 | Ranki et al. |
| 5,437,983 A | 8/1995 | Watts et al. |
| 6,299,881 B1 * | 10/2001 | Lees et al. ............... 424/194.1 |

FOREIGN PATENT DOCUMENTS

| EP | 0 276 302 | 8/1988 |
| EP | 0 420 260 | 4/1991 |
| EP | 0 446 260 | 3/1994 |
| FR | 2 422 956 | 11/1979 |
| WO | WO 88/01302 | 2/1988 |

OTHER PUBLICATIONS

Gilles et al. "Stability of Water-Soluble Carbodiimides in Aqueous Solution" Anal. Biochem. (1990) 184: 244-248.*

Situmorang et al. "Immobilization of enzyme throughout a polytyramine matrix: a versatile procedure for fabricating biosensors". *Analytical Chimica Acta*, vol. 374, pp. 211-223 (1999).

Bastos-Gonzalez et al. "Carboxylated latexes for covalent coupling antibodies, I". *Journal of Colloid and Interface Science*, vol. 176, pp. 232-239 (1995).

Sudi et al. "Preparation, characterization, and application of a novel immobilized carboxypeptidase B." *Applied Biochemistry and Buitechnology*, vol. 22, pp. 31-43 (1989).

Dagenais et al. "Direct covalent attachment of small peptide antigens to enzyme-linked immunosorbent assay plates using radiation and carbodiimide activation". *Analytical Biochemistry*, vol. 222, pp. 149-155 (1994).

Bieniarz et al. "Extended length heterobifunctional coupling agents for protein conjugations." *Bioconjucate Chemistry*, vol. 7, pp. 88-95 (1996).

Wong. "Zero-length cross-linking reagents". *Chemistry of Protein Conjucation and Cross-Linking*. CRC Press, pp. 195. (1991).

Gilles et al. "Stability of water-soluble carbodiimides and aqueous solution". *Analytical Biochemistry*, vol. 184, pp. 244-248 (1990).

Bangs Laboratories, Inc. "Tech Note #13c Covalent coupling protocols".

Lundblad et al. *Chemical Reagents for Protein Modification*, vol. 2, Chapter 4, CRC Press, Boca Raton (1984).

Mikolajczyk et al. "Recent Developments in the carbodiimide chemistry". *Tetrahedron*, vol. 37, pp. 233-284 (1981).

Staros. "N-hydroxysulfosuccinimide active esters: bis N-hydroxysulfosuccinimide esters of two dicarboxylic acids are hydrophilic, membrane-impermeant, protein cross-linkers". *Biochemistry*, vol. 21, pp. 3950-3955 (1982).

O'Sullivan et al. "Comparision of two methods of preparing enzyme-antibody conjugates: application of these conjugates for enzyme immunoassay". *Analytical Biochemistry*, vol. 100, pp. 100-108 (1979).

(Continued)

Primary Examiner—Jean C. Witz
Assistant Examiner—Susan Hanley
(74) Attorney, Agent, or Firm—Merchant & Gould P.C.

(57) ABSTRACT

The invention relates to a method of immobilizing an affinity reagent or affinity reagents on a hydrophobic solid phase which can be used in biological assays for analyte detection. The invention relates more particularly to a method of immobilizing an affinity reagent on a hydrophobic solid phase functionalized by a carboxyl group, said method comprising a step for activation of said solid phase and a step for coupling of the affinity reagent to said solid phase, characterized in that the step for activation of said solid phase uses a combination of a carbodiimide and a phosphate buffer in the presence of a co-activator and in an acid medium, and in that the coupling step is performed in a basic medium.

Figure 1:
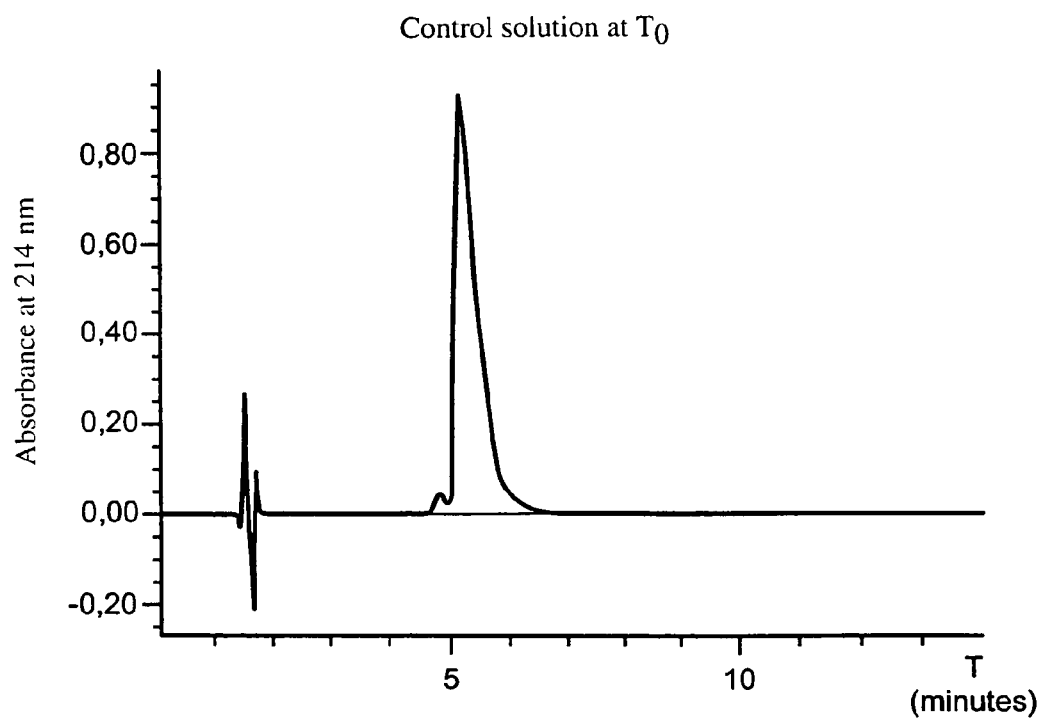

The invention further relates to the reactive complexes obtained by this method and to their use in immunoassay kits, hybridization kits or enzymatic assay kits.

11 Claims, 2 Drawing Sheets

OTHER PUBLICATIONS

Abdella et al. "A new cleavable reagent for cross-linking and reversible immobilization of proteins". *Biochemical and Biophysical Research Communications*, vol. 97, No. 3, pp. 734-742 (1979).

Ottewill et al. "Studies on the preparation and characterization of monodisperse polystyrene lattices". *Kolloide-Zeitchrift und Zeitchrift fur Polymere*, vol. 215, pp. 161-166 (1967).

Atherton et al. "Flourenylmethoxycarbonyl-polyamide solid phase peptide synthesis-general principles and development". in *Solid Phase Peptide Synthesis: A Parctical Approach*, IRL Press, Oxford University Press, pp. 25-34 (1989).

Sackrison. "Covalent coupling to latex particles and diagnosing development using microsphere". Presented at Diagnostic Applications of Latex Technology, Theory and Practice, Sponsored by Bangs Laboratories, Inc. (1997).

Urdea et al. "Branched DNA amplification mulimers for the sensitive, direct detection of human hepatitis viruses". *Nucleic Acids Research, Series 24*, pp. 197-200 (1991).

Sanchez-Pescador et al. "Rapid chemiluminescent nucleic acid assys for detection of TEM-1 β-Lactamase-mediated penicillin resistance in *Neisseria gonorrhoeae* and other bacteria". *Journal of Clinical Microbiology*, vol. 26, No. 10, pp. 1934-1938 (1988).

Langdale et al. "A rapid method of gene detection using DNA bound to sephacryl". *Gene*, vol. 36, pp. 201-210 (1985).

Ranki et al. "Sandwich hybridization as a convenient method for the detection of nucleic acids in crude samples". *Gene*, vol. 21, pp. 77-85 (1983).

Dunn et al. "A novel method to map transcripts: Evidence for homology between an adenovirus mRNA and discrete multiple regions of the viral genome". *Cell*, vol. 12, pp. 23-36 (1977).

Cook et al. "Synthesis and hybridization of a series of biotinylated oligonucleotides". *Nucleic Acids Research*, vol. 16, No. 9, pp. 4077-4095 (1988).

Nagata et al. "Quantification of picogram levels of specific DNA immobilized in microtiter wells". *FEBS Letters*, vol. 183, No. 2, pp. 379-382 (1985).

* cited by examiner

METHOD FOR IMMOBILIZATION OF (AN) AFFINITY REAGENT(S) ON A HYDROPHOBIC SOLID PHASE

The invention relates to a method for immobilisation of (an) affinity reagent(s) on a hydrophobic solid phase which can be used in biological assays for analyte detection, to the reactive complexes obtained by this method and to the use of said complexes in biological assay kits.

Biological analysis assays which use reagents with a mutual affinity have been known for decades. Said reagents will hereafter be referred to by the term 'affinity reagents' or 'affinity pair reagents'. Thus it is known how to search for and detect one member of an affinity pair by means of the other. Biological assays which utilize an affinity reaction between affinity reagents, or 'affinity assays', include enzymatic analyses utilizing e.g. an enzyme and its substrate, qualitative or quantitative immunoassays initiated by the pioneering work of Berson and Yalow (1959) and involving the reaction of an antibody with the corresponding antigen or hapten, more recently nucleic acid hybridization assays utilizing a target oligo-nucleotide or poly-nucleotide with a complementary nucleotide probe capable of hybridizing specifically therewith, etc.

Since the 1960s attempts have been made to use reactive solid phases (or solid supports) in affinity assays requiring a separation of the free complexes and the bound complexes obtained, in order to simplify this separation step.

Affinity reagents can be immobilized on a solid phase by covalent coupling, for example with the aid of glutaraldehyde. It is also known, since the work of Catt and Tregear in 1967, to immobilize an affinity reagent on a solid phase by simple passive adsorption.

Immobilization by passive adsorption has the advantage of simplicity, but it can cause inappropriately immobilized reagent to be released into a liquid medium.

Solid-phase covalent couplings generally have the advantage of producing the final reagent with a greater stability, but they also enable more affinity reagent to be immobilized on a solid support. There are a large number of solid-phase covalent coupling modes and agents currently available: non-limiting examples which may be mentioned are couplings with glutaraldehyde, cyanogen bromide and carbodiimides, in the presence or absence of a co-activator such as DMAP (dimethylaminopyridine), HOBt (1-hydroxybenzotriazole), N-hydroxysuccinimide or s-NHS (sulfo-N-hydroxysuccinimide), which are well known to those skilled in the art.

The different protocols for immobilizing an affinity reagent on a solid phase by covalent coupling are carried out in one, two or even three steps. In one-step couplings, all the ingredients are brought into contact with one another. Two-step couplings generally involve a first step in which the solid support is activated by a so-called 'activator', then washed to remove any excess unreacted activator, and finally brought into contact with the affinity reagent, enabling the actual coupling to be carried out in a second step.

Numerous solid phases or supports are known and used: hydrophilic solid phases (for example Sephadex® marketed by Pharmacia) and hydrophobic solid phases (for example polypropylene, polystyrene, latices, etc.). The latter are generally rendered reactive via functional groups grafted on beforehand, such as amine, carboxyl, tosyl, aldehyde, hydroxyl, thiol, chloromethyl, hydrazide and other groups.

Different techniques have been proposed for the covalent coupling of affinity reagents to hydrophobic solid phases functionalized by a carboxyl group: various combinations of buffer and activator are used such as the combination of MES (2-[N-morpholino]ethanesulfonic acid) with a carbodiimide. An example which may be mentioned is the covalent coupling of antibodies to carboxylic latices in the presence of MES and EDC (1-ethyl-3-[3-dimethylaminopropyl]carbodiimide), described by D. Bastos-Gonzalez et al., J. of Colloid and Interface Science, 176, 232–239 (1995), or by C. Bieniarz et al., Bioconjugate Chem., 1996, 7, 88–95.

However, it has long been known that the combination of phosphate buffer and carbodiimide—as activator—is to be avoided because carbodiimides have the disadvantage of activating phosphates as well and hence of losing a large part of their reactivity. This results simultaneously in an insufficient efficacy of covalent coupling, a high proportion of passive adsorption and, as a consequence, an instability of the products obtained (Wong, S. in 'Chemistry of protein conjugation and crosslinking', chapter 6, page 196 (1991), and M. A. Gilles et al., Analytical Biochemistry, 184, 244–248 (1990)).

Bangs (Bangs Laboratories Inc., Tech. Note #13c, Covalent coupling protocols, page 3) has proposed a protocol for the activation of hydrophobic solid phases functionalized by a carboxyl group with the aid of the carbodiimide EDC in aqueous solution, but the results obtained are far from satisfactory from the point of view of coupling efficacy. In fact, the coupling is not quantitative and the proportion of passive adsorption is high compared with the covalent coupling (cf. Example 1 below).

In general, with all the techniques of the prior art aimed at using covalent coupling to immobilize an affinity reagent on a hydrophobic solid phase functionalized by a carboxyl group, it is observed that the actual covalent coupling between the affinity reagent and the solid phase is simultaneously accompanied by the unwanted co-existence of a substantial degree of fixing of said affinity reagent to said solid phase by passive adsorption. In other words, these techniques have the disadvantage of being incapable of allowing the desired maximum degree of covalent fixing. As passive adsorption cannot be controlled in favor of covalent coupling, it follows that these techniques do not make it possible to optimize the covalent fixing of the affinity reagent or hence to obtain reproducible covalent couplings. Consequently they give rise to products which are unstable over time.

There is therefore a genuine need for a method of immobilizing an affinity reagent on a hydrophobic solid phase functionalized by a carboxyl group which makes it possible reproducibly to control and optimize the covalent character of the coupling while at the same time minimizing the possibility of simultaneous passive adsorption.

It has now been found, surprisingly, that it is possible reproducibly to control and optimize the covalent character of a reaction for immobilizing an affinity reagent on a hydrophobic solid phase functionalized by a carboxyl group with the aid of a combination of a carbodiimide and a phosphate buffer as activator.

The invention therefore relates to a method of immobilizing an affinity reagent on a hydrophobic solid phase functionalized by a carboxyl group, said method comprising a step for activation of said solid phase and a step for coupling of the affinity reagent to the solid phase, and being characterized in that the step for activation of said solid phase uses a combination of a carbodiimide and a phosphate buffer in an acid medium, in the presence of a co-activator, and in that the step for coupling of the affinity reagent is performed in a basic medium.

Any carbodiimide used in this field as a carboxyl group activator, and in the field of peptide synthesis, can be used for the purposes of the invention.

Examples of carbodiimides are described especially by Lundblad, R. L. et al., Chemical Reagents for Protein Modification, vol. 2, chap. 4, CRC Press; Boca Raton, Fla. and Marion Mikolajczyk et al., Tetrahedron, vol. 37, pp. 233–284 (1981).

CMC (N-cyclohexyl-N'-(2-morpholinoethyl)carbodiimide methyl-p-toluenesulfonate) and EDC (1-ethyl-3-[3-dimethylaminopropyl]-carbodiimide) may be mentioned in particular among the carbodiimides which can be used as activators within the framework of the invention, CMC being particularly preferred.

The carbodiimide must be used in excess relative to the COOH group. The amount used is advantageously 20 to 50 molar equivalents per COOH group.

'Phosphate buffer' is understood within the framework of the invention as meaning any conventional phosphate buffer (sodium and/or potassium) used at a concentration generally ranging from 30 to 200 mM, 50 mM phosphate buffer being more particularly preferred.

It is possible to use any co-activator employed in this field. Examples of co-activators are described especially by Staros, J. V., Biochemistry, 21, 3950–3955 (1982); O'Sullivan, M. J. et al., Anal. Biochem., 100, 100–108 (1979); Abdella, P. M. et al., Biochem. Biophys. Res. Commun., 87, 734–742 (1979).

s-NHS (sulfo-N-hydroxysuccinimide), HOBt (1-hydroxybenzotriazole) and N-hydroxysuccinimide can be employed in particular among the co-activators which can be used according to the invention, s-NHS (sulfo-N-hydroxysuccinimide) being particularly preferred.

Like the carbodiimide, the co-activator must be used in excess relative to the COOH group. The amount used is advantageously 3 to 10 molar equivalents per COOH group.

'Acid medium' in the activation step of the method of the invention is understood as meaning any medium with a pH ranging from about 4 to about 6.5, a pH of 6 being more particularly preferred, the acid character of said medium being conferred by the phosphate buffer.

'Basic medium' in the coupling step of the method of the invention is understood as meaning a medium with a pH ranging from about 7.2 to about 10.5, a medium containing 50% of a buffer of pH 8.5 being more particularly preferred.

The basic character of the medium is obtained by using appropriate conventional buffers, for example a borate buffer or a phosphate buffer/borate buffer mixture.

Thus, in a preferred embodiment of the invention, the step for activation of the solid phase uses a combination of 20 to 50 molar equivalents per COOH group of CMC, in 30–200 mM phosphate buffer, in the presence of 3 to 10 molar equivalents per COOH group of sulfo-N-hydroxysuccinimide co-activator, in an acid medium with a pH ranging from about 4 to about 6.5, and the coupling is carried out in a basic medium with a pH ranging from about 7.2 to about 10.5.

In a particularly preferred embodiment of the invention, the step for activation of the solid phase uses a combination of 30 molar equivalents per COOH group of CMC, in 50 mM $KH_2PO_4$ phosphate buffer, in the presence of 5 molar equivalents per COOH group of sulfo-N-hydroxysuccinimide co-activator, at pH 6, and the coupling is carried out in a medium containing 50% of a borate buffer of pH 8.5.

The judicious combination of activation parameters—carbodiimide, phosphate buffer, co-activator and acid pH—associated with the coupling conditions described above is essential for implementation of the method of the invention.

The affinity reagents which can be immobilized within the framework of the invention are any compounds which have an amine group or can be artificially provided with an amine group. Such affinity reagents which may be mentioned are proteins, peptides, immunoglobulins, antigens, haptens, antibodies, enzymes, enzyme substrates, oligonucleotides, polynucleotides, etc., as well as any other biological reagent known to those skilled in the art.

'Hydrophobic solid phase' is understood in the present description as meaning solid phases consisting of hydrophobic polymers commonly used in this field, for example polypropylenes and vinylaromatic polymers such as polystyrenes, and especially the latices of these polymers. These solid phases are functionalized by a carboxyl group using the techniques well known to those skilled in the art. In this connection, reference may be made e.g. to the article by Ottewill R. H. et al. in Kolloid Zu Z. Polymere, 215, 161–166 (1967).

Among the hydrophobic solid phases functionalized by a carboxyl group which can be used according to the invention, there may be mentioned latex particles, for example those known under the mark Estapor® (Prolabo, France), Dynabeads® magnetic particles from Dynal, Polybead® microspheres from Polysciences, Inc., and equivalents thereof, etc.

The invention further relates to the reactive solid complexes obtainable by the method according to the invention, such as solid phase/antigen complexes, solid phase/hapten complexes, solid phase/antibody complexes, etc., which can be used in immunoassays, solid phase/oligonucleotide or polynucleotide complexes, which can be used in nucleic acid hybridization assays, amplification assays, etc., solid phase/enzyme complexes or solid phase/enzyme substrate complexes, etc.

The invention further relates to the use of these complexes in kits for biological assays, non-restricting examples being immunoassays, nucleic acid hybridization assays, nucleic acid amplification assays, enzymatic assays, etc., known to those skilled in the art, whether qualitative or quantitative.

The invention will be understood more clearly with the aid of the following Examples, which are given simply by way of illustration and must not in any way be understood as restricting the scope of the invention.

EXAMPLE 1

Coupling of a Peptide to Carboxylic Beads a) Reagents
a1) Carboxylic Beads

Magnetic carboxylic latex beads produced by Prolabo, France (reference Estapor M1,070/60) were used as the hydrophobic solid phase carrying a carboxyl group. They consist of polydisperse particles of polystyrene and iron oxide, functionalized by COOH groups. The solid phase used has the following characteristics: mean diameter (0.8 µm), percentage of iron (62%), degree of functionalization (150 µeq COOH/g). It takes the form of a 0.1 g/ml aqueous suspension.

All the bead washing steps are performed as follows:

In each experiment the magnetic beads present in the test tubes are separated from the solutions with a magnetized support. The supernatants are removed with a pipette, the magnetic beads being held in said tubes by the magnetized support. After each addition of a new solution or new buffer, the beads are resuspended by vortexing for about 10 seconds.

A wash comprises the addition of the washing solution, the resuspension of the beads and the removal of this solution by magnetization.

a2) Peptide

The peptide of 17 amino acids having the following sequence was used in this Example: KGSYSVDHFR-WGRVSG-NH2. (SEQ. ID NO. 1)

This peptide was prepared by the procedure described by E. Atherton and R. L. Sheppard in 'Solid phase peptide synthesis, a practical approach', IRL PRESS (1989), Oxford University Press, pp. 25–34.

The phosphate buffer solution used was a 50 mM aqueous solution of $KH_2PO_4$ of pH 6.

All the operations were carried out at room temperature, i.e. at 19–24° C.

b) Immobilization of the Peptide on the Carboxylic Beads b1) Covalent Coupling of the Peptide to the Carboxylic Beads Step 1: Washing of the Carboxylic Beads:

50 μl of magnetic carboxylic latex beads in a test tube are washed twice with 750 μl of 0.1 mM NaOH of pH 9, once with 750 μl of double-distilled water and finally once with 750 μl of phosphate buffer.

Step 2: Activation of the Carboxylic Beads:

250 μl of phosphate buffer, 200 μl (30 eq/COOH group) of an aqueous solution of CMC [N-cyclohexyl-N'-(2-morpholinoethyl) carbodiimide methyl-p-toluenesulfonate (Fluka)] and 50 μl (5 eq/COOH) of an aqueous solution of s-NHS [sulfo-N-hydroxysuccinimide (Pierce)] are added to the residue of washed beads obtained in step 1.

The reaction mixture is incubated for 1 hour at room temperature, with shaking. The beads are then washed with 500 μl of phosphate buffer.

Step 3: Coupling of the Peptide to the Beads:

250 μl of phosphate buffer and 250 μl of a 37.5 mM borate/50 mM NaCl buffer solution of pH 8.5, containing 0.25 eq (based on the COOH groups) of the peptide described in section a2), are added to the residue of activated beads obtained in step 2.

The reaction mixture is incubated for 1 hour at room temperature, with shaking. The beads are separated by magnetization and the supernatant is retained for determination by HPLC (cf. section c) below). After washing, the beads are kept in PBS of pH 7.4 or any other suitable equivalent buffer.

b2) Passive Adsorption of the Peptide on the Carboxylic Beads

A coupling of the 'passive' type—also called 'passive adsorption'—is performed using exactly the same reagents as above except that the activator and coupling agent, CMC and s-NHS, are omitted. After coupling of the 'passive' type, the beads are separated by magnetization and the supernatant is retained for determination by HPLC (cf. section c)).

c) Calculation of the Covalent Coupling Yield and Evaluation of the Passive Coupling by HPLC The couplings are followed by reversed-phase high performance liquid chromatography (HPLC) on an apparatus (e.g. Waters) with an apolar stationary phase (C18) and a polar mobile phase (gradient: acetonitrile/0.08% aqueous TFA—0.1% TFA).

At the end of each coupling (covalent or passive), 30 μl of the supernatant obtained in section b1) or b2) are injected into the HPLC apparatus.

An identical volume of 'control solution' (i.e. the same peptide solution (in 250 μl of 37.5 mM borate/50 mM NaCl buffer of pH 8.5 and 250 μl of phosphate buffer) as that used in the couplings except that it is not coupled to the magnetic beads) is also injected into the HPLC apparatus.

A BRIEF DESCRIPTION OF THE DRAWINGS

Figure 2:
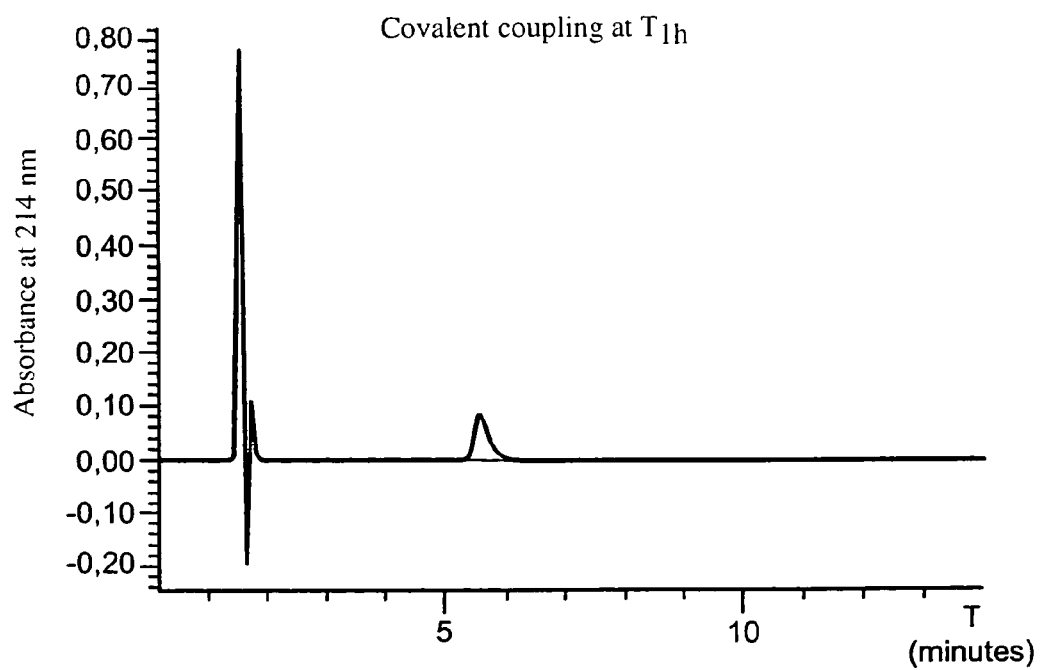
Figure 3:
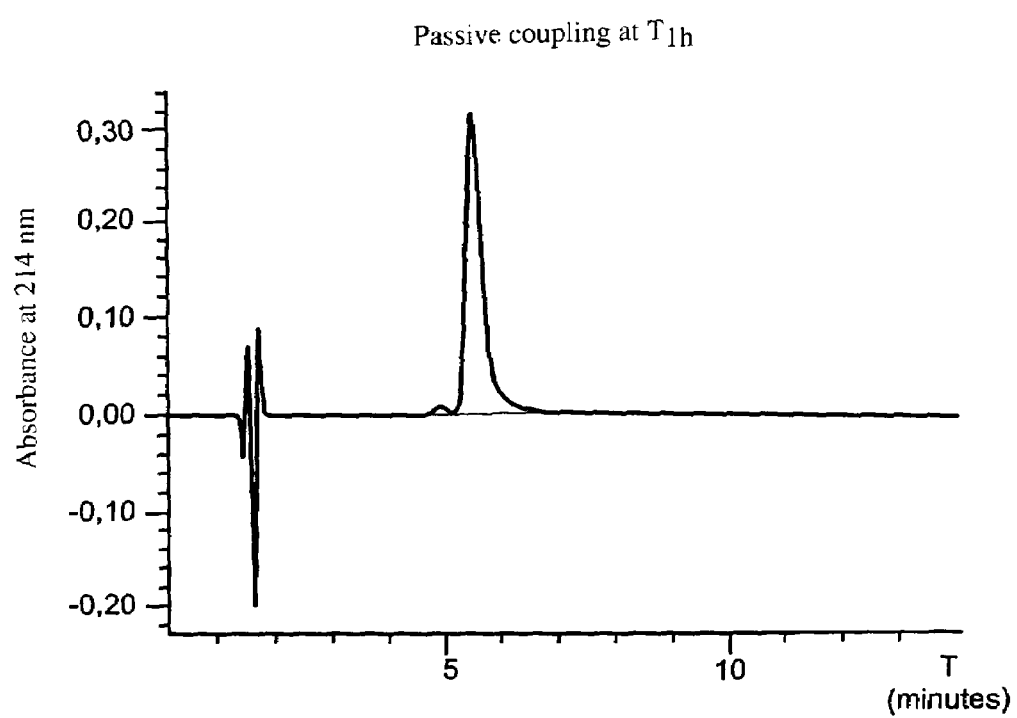

The HPLC chromatograms, obtained by measuring the absorbance at 214 nm as a function of the time T expressed in minutes, are shown in FIGS. 1 to 3. The chromatogram of FIG. 1 shows the peak obtained with a control solution (assay without coupling to the magnetic beads) at $T_0$, said solution serving as a reference by indicating the total amount of peptide introduced.

The chromatogram of FIG. 2 shows the peak obtained with a supernatant taken at $T_{0+1\ hour}$ at the end of the covalent coupling described in section b1).

The chromatogram of FIG. 3 shows the peak obtained with a supernatant taken at $T_{0+1\ hour}$ at the end of the passive adsorption described in section b2).

For each chromatogram the peak area is integrated by a software program (e.g. Millenium software). This measures the area A0 for the control solution, the area A1 for the covalent coupling and the area A2 for the 'passive type' coupling.

The coupling yield is thus evaluated by a back determination, known to those skilled in the art, using the following formula:

$$\% \text{ covalent coupling} = \frac{(A0 - A1)}{A0} \times 100$$

$$\% \text{ 'passive' coupling} = \frac{(A0 - A2)}{A0} \times 100$$

d) Comparison of the Coupling According to the Invention with Couplings According to the Prior Art The study was carried out on 3 protocols of the prior art and the protocol according to the invention. A coupling under 'passive' conditions, omitting the coupling agent and activator, was performed in parallel for all the protocols. The yields of covalent coupling and passive coupling were evaluated by the method described in c).

Protocols of the Prior Art:

'Bangs' protocol, Bangs Laboratories Inc., Tech. note #13c, Covalent coupling protocols, page 3.

The beads were washed in a preactivation buffer (50 mM phosphate buffer of pH 4.5) and then activated with an aqueous solution of EDC in the presence of a small percentage (20%) of preactivation buffer. The coupling was performed in 0.2 M borate buffer of pH 8.5. After coupling, the unreacted carboxyl groups were blocked with ethanolamine solution. The beads were kept in a buffer containing BSA, glycine, Tween® detergent and sodium azide.

J. Sackrison protocol, Covalent coupling to latex particles and diagnostic development using microspheres, the latex course, 1997.

The beads were washed several times with a 10 mM borate buffer solution of pH 8.5, with a 10 mM sodium acetate solution of pH 5.0 and with a 50 mM diethanolamine solution of pH 10.2 and then activated with a solution of CMC in 50 mM diethanolamine buffer of pH 10.2. The coupling was performed in 100 mM phosphate/150 mM NaCl buffer of pH 7.4.

protocol 1 described by D. Bastos-Gonzalez et al., J. of Colloid and Interface Science, 176, 232–239, 1995.

Latex beads were added to a buffer solution (MES) of pH 5.6. The coupling was performed in a weakly acidic medium (in MES buffer of pH 5.6). An aqueous solution of EDC was added and the sample was then incubated at room temperature. After coupling, the excess carboxyl groups were blocked by treatment with ethanolamine.

The results obtained by HPLC determination are indicated in Table I in the form of the coupling yields (%) and the difference between covalent coupling and passive adsorption ($\Delta$):

TABLE I

| Protocol | % of passively coupled peptide | % of covalently coupled peptide | $\Delta$ (covalent − passive) |
|---|---|---|---|
| Bangs | 47 | 57 | 10 |
| Latex course (J. Sackrison) | 80 | 82 | 2 |
| Protocol 1 (D. Bastos-Gonzalez et al.) | 8 | 13 | 5 |
| Protocol according to the invention | 54 | 100 | 46 |

The best performance characteristics are obtained with the coupling protocol according to the invention when compared with those obtained with the protocols of the prior art; thus, with the coupling protocol according to the invention, the covalent coupling yield is quantitative (100%) and the difference between covalent coupling and passive coupling is appreciable, in contrast to the protocols of the prior art, where the difference between the 2 forms of coupling is relatively insignificant.

e) Reproducibility of the Coupling Method According to the Invention

The reproducibility of the coupling method according to the invention was studied on the one hand by performing 3 couplings on one and the same batch of beads, and on the other hand by performing a coupling on a different batch of beads.

A covalent coupling according to the protocol described in section b1) (above) and a coupling of the 'passive' type according to the protocol described in section b2) (above) were performed in parallel in each experiment. Calculation of the coupling yield and evaluation of the passive coupling were determined according to protocol c) above.

The results obtained by HPLC determination are indicated in Table II in the form of the coupling yields (%) and the difference between covalent coupling and passive adsorption ($\Delta$):

TABLE II

| Batch of beads | % of passively coupled peptide | % of covalently coupled peptide | $\Delta$ (covalent − passive) |
|---|---|---|---|
| 477 | 52 | 98 | 46 |
| 477 | 54 | 100 | 46 |
| 477 | 58 | 100 | 42 |
| 583 | 56 | 93 | 37 |

These results show that the reproducibility is excellent with one and the same batch (batch 477). With a different batch (batch 583) the coupling yield is totally acceptable and comparable to the yield obtained with the first batch.

EXAMPLE 2 a) Coupling of Bovine Serum Albumin (BSA) to Magnetic Carboxylic Beads

175 μg of BSA (Pantex) are coupled under the conditions described in section b1) of Example 1. The actual coupling reaction is carried out for 22 hours (instead of 1 hour) at room temperature.

A passive adsorption is performed under the same conditions except that the coupling agent, CMC, and the co-activator, s-NHS, are omitted. After coupling, the beads are separated by magnetization and the supernatant is retained for determination by HPLC.

b) Comparison of the BSA Coupling According to the Invention with Couplings of the Prior Art The protocol according to the invention was compared with 2 protocols of the prior art, namely the 'Bangs' protocol and the 'latex course' protocol (J. Sackrison).

The covalent coupling and passive adsorption yields using the 3 protocols were evaluated by the method described in section c) of Example 1.

The results obtained by HPLC determination are indicated in Table III in the form of the coupling yields (%) and the difference between covalent coupling and passive adsorption ($\Delta$):

TABLE III

| Protocol | % of passively coupled BSA | % of covalently coupled BSA | $\Delta$ (covalent − passive) |
|---|---|---|---|
| Bangs | 13 | 17 | 4 |
| Latex course (J. Sackrison) | 31 | 34 | 3 |
| Protocol according to the invention | 25 | 65 | 40 |

The results show the superiority of the protocol of the invention compared with the protocols of the prior art since the former affords a much higher coupling $\Delta$ (covalent−passive).

EXAMPLE 3

Application to a Diagnostic Test for the Detection of Anti-HIV Antibodies

As indicated below, the beads obtained by the method of the invention were used to detect anti-HIV antibodies in a known ELISA test, namely the Access® HIV 1–2 New test marketed by and available from Bio-Rad Laboratories, Marnes la Coquette, France, catalog number 34 020, in which an anti-HIV-2-specific antibody is sandwiched between a capture antigen immobilized on magnetic beads and an antigen labeled with an enzyme. Disclosure and measurement of the signal are effected by adding a chemoluminescent enzyme substrate and reading off the luminescence generated.

a) Materials and Methods a1) Capture Antigen (Peptide)

A peptide of 27 AA containing the essential immunodominant epitope, namely the heptapeptide CAFRQVC (SEQ. ID NO. 2) of gp36 of HIV-2, was synthesized by the above-mentioned method of E. Atherton and R. L. Sheffard and then coupled to BSA by covalent coupling with the aid of the homobifunctional reagent bis(sulfosuccinimyl) suberate. The BSA/HIV-2 peptide conjugate obtained is hereafter referred to as 'BSA/HIV-2'.

a2) Immobilization of the Capture Antigen

The above BSA/HIV-2 conjugate was then coupled to magnetic carboxylic latex beads (Estapor) according to the covalent coupling protocol of the invention and according to a protocol of the prior art.

12 µg of BSA/HIV-2 conjugate were coupled to 100 µl of beads by the method described in Example 1b).

12 µg of BSA/HIV-2 conjugate were coupled to 100 µl of beads by a method of the prior art (protocol 1 of Bastos-Gonzalez: cf. Example 1d)).

The resulting magnetic beads carrying BSA/HIV-2 peptide are hereafter referred to as 'BSA/HIV-2 beads'.

a3) Disclosure Antigen

The same peptide of 27 AA containing the essential immunodominant epitope, namely the heptapeptide CAFRQVC (SEQ. ID NO. 2) of gp36 of HIV-2, as that used in a1) above was coupled to alkaline phosphatase (hereafter referred to as 'ALP'), from Biozyme, by covalent coupling with the aid of the homobifunctional reagent bis(sulfosuccinimyl) suberate. The HIV-2 peptide/ALP conjugate obtained is hereafter referred to as 'peptide/ALP'.

a4) Detection of the Signal

Disclosure is obtained using a dioxetane-based substrate specific for alkaline phosphatase. The signal is read off on an Access® luminometer available from Bio-Rad Laboratories, France. The signal is expressed in RLU (Relative Luminescence Units).

a5) Samples

The assay was performed using human sera positive in anti-HIV-2 antibodies, diluted in negative human serum (qc1, qc2, qc3), and a serum negative in anti-HIV antibodies (C0).

b) Assay Protocol

Two series were carried out in parallel.

b1) 50 µl of serum were brought into contact with 50 µg of BSA/HIV-2 beads obtained according to the covalent coupling protocol of the invention, and with 350 µl of peptide/ALP conjugate. The mixture was incubated for 20 minutes at 37° C., the beads were then separated by magnetization and the supernatant was removed.

200 µl of substrate were added and incubation was carried out for 5 minutes at 37° C.

The reading was taken and the RLU recorded. The results are expressed as the 'Signal/C0' RLU ratio: cf. Table IV.

b2) 50 µl of serum were brought into contact with 50 µg of BSA/HIV-2 beads obtained according to protocol 1 of Bastos-Gonzalez, and with 350 µl of peptide/ALP conjugate.

The remainder of the protocol is identical to that of procedure b1) above.

c) Results and Comparison with the Prior Art

The results obtained with the coupling according to the invention and those obtained with the coupling according to protocol 1 are indicated in Table IV:

TABLE IV

| Serum tested | Protocol 1 | | Protocol according to the invention | |
|---|---|---|---|---|
| | RLU | SIGNAL/C0 | RLU | SIGNAL/C0 |
| C0 | 15,205 | 0.98 | 10,767 | 1.00 |
| | 15,741 | 1.02 | 10,771 | 1.00 |
| mean | 15,473 | | 10,769 | |
| qc1 | 171,048 | 11.05 | 1,894,150 | 175.89 |
| | 168,968 | 10.92 | 1,904,600 | 176.86 |
| qc2 | 15,517 | 1.00 | 181,888 | 16.89 |
| | 15,444 | 1.00 | 183,826 | 17.07 |
| qc3 | 12,731 | 0.82 | 80,437 | 7.47 |
| | 12,591 | 0.81 | 80,462 | 7.47 |

The results show that, for the positive samples, the 'Signal/C0' ratio obtained by the protocol according to the invention is considerably greater than that obtained by protocol 1 of the prior art. This translates into a much better immuno-reactivity and a better analytical sensitivity and very clearly reflects the fact that the coupling method according to the invention has afforded an optimum covalent coupling compared with protocol 1.

EXAMPLE 4

Stability Tests on Magnetic Carboxylic Latex Beads Coated with BSA/HIV-2 Conjugate ('BSA/HIV-2 beads') of the Invention A long-term stability study—7 months, 12 months and 18 months at +4° C.—was carried out using the protocol of Example 3 for BSA/HIV-2 beads (batch C7P184A obtained in Example 3 from beads of initial batch 477, cf. above). Table V summarizes the results obtained, which show that the batch did not significantly lose immunoreactivity in 18 months at +4° C. In the results in Table V below, the expression 'SIGNAL/C0' has been replaced by the abbreviated form 'S/C0' for the sake of presentation.

TABLE V

| Serum tested | T0 | | T = 7 months | | T = 12 months | | T = 18 months | |
|---|---|---|---|---|---|---|---|---|
| | RLU | S/C0 | RLU | S/C0 | RLU | S/C0 | RLU | S/C0 |
| C0 | 12,144 | | 13,962 | | 12,898 | | 12,768 | |
| | 11,866 | | 13,692 | | 13,855 | | 12,773 | |
| | | | | | 13,586 | | | |
| mean | 12,005 | 1.00 | 13,827 | 1.00 | 13,446 | 1.00 | 12,771 | 1.00 |
| qc2 | 139,029 | | 184,633 | | 170,026 | | 182,311 | |
| | 141,796 | | 185,985 | | 173,015 | | 182,952 | |
| | | | | | 173,033 | | | |
| mean | 140,413 | 12 | 185,309 | 13 | 172,025 | 13 | 182,632 | 14 |
| qc1 | 1,732,230 | | 2,166,040 | | 2,159,050 | | 2,076,950 | |
| | 1,799,880 | | 2,142,940 | | 2,279,010 | | 2,127,930 | |
| | | | | | 2,102,220 | | | |
| mean | 1,766,055 | 147 | 2,154,490 | 156 | 2,180,093 | 162 | 2,102,440 | 165 |

These results clearly show that the method according to the invention affords complexes of affinity reagents (immobilized on a hydrophobic solid phase functionalized by a carboxyl group) which have a high stability over time.

EXAMPLE 5

Covalent Coupling of Nucleic Acid to Magnetic Carboxylic Latex Beads a) Materials and Methods 5×SSC and 2×SSC buffers are prepared by the method described in Maniatis T. et al., Molecular Cloning. A laboratory manual, Cold Spring Harbor laboratory, New York (1982).

Probes (DNA) functionalized in the 5' position by an amine group are obtained via an automatic synthesizer using the commercial reagent aminolink 2 from Perkin Elmer, and are referred to below as 5'-$NH_2$ probes.

The analyte used is either RNA or DNA. The performance characteristics of the probe coupling are evaluated in a sandwich hybridization format on an Access® apparatus from Beckman.

An analyte-specific DNA probe is coupled to magnetic particles according to the protocol described in b) below. It serves to capture the analyte (capture probe).

Disclosure is effected with the aid of an analyte-specific detection probe (different from the first probe) labeled, e.g. with the enzyme alkaline phosphatase, by methods known to those skilled in the art.

Examples of the non-radioactive labeling of probes are described e.g. in patent FR 78.10975, by M. S. Urdea et al., Nucleic Acids Symp. Ser., 24, 1991, 197–200, or by R. Sanchez-Pescador, J. Clin. Microbiol., 26, 1988, 1934–1938.

The yield of the covalent coupling of nucleic acid to magnetic carboxylic latex beads is evaluated as in Example 1 by HPLC under conditions adapted to nucleic acids: for example stationary phase (C18) and mobile phase (gradient of buffer A: $10^{-2}$ M triethylammonium acetate, and buffer B: acetonitrile/A: 95/5).

b) Covalent Coupling of a 5'-$NH_2$ Probe to Magnetic Carboxylic Latex Beads

20 µg of a 5'-$NH_2$ probe (i.e. a probe carrying an $NH_2$ group in the 5' position) are coupled to 200 µl of Estapor M1–070/60 magnetic carboxylic latex beads under similar conditions to those of Example b1).

The beads are then washed twice with 500 µl of 5×SSC buffer and twice with 500 µl of 2×SSC buffer. They are kept in 2×SSC buffer containing 0.02% of $NaN_3$.

Hybridization assay: Hybridization of the capture and detection probes with the analyte can be effected separately (in two steps) or simultaneously (in one step), especially by one of the methods described by Langhale and Malcolm, Gene, 36, 1985, 201–210, by Ranki et al., Gene, 21, 1993, 77–85, by Dunn and Hassel, Cell, 12, 1977, 23–36, or by Ranki and Soderlund in patents U.S. Pat. No. 4,486,539 and U.S. Pat. No. 4,563,419.

Those skilled in the art will be capable of reproducing hybridization experiments without difficulty and comparing the coupling method according to the invention with coupling techniques of the prior art. Coupling techniques of the prior art which may be mentioned are the fixing of the capture probe to the solid support by well-known methods, especially by passive adsorption or covalent coupling (Cook et al., Nucleic Acids Res., 16, 1988, 4077–4095; Nagata et al., FEBS Lett., 183, 1985, 379–382; M. Longlaru et al., EP 420 260 A2; T. Gingeras et al., EP 276 302; E. Kornes and L. M. Kornes, EP 446 260).

The invention claimed is:

1. Method of immobilizing an affinity reagent on a hydrophobic solid phase functionalized by a carboxyl group, said method comprising a step for activation of said solid phase and a step for coupling of the affinity reagent to said solid phase, wherein the step for activation of said solid phase uses a combination of a carbodiimide and a phosphate buffer in the presence of a co-activator and in an acid medium with a pH ranging from about 4 to about 6.5, and the coupling step is performed in a basic medium with a pH ranging from about 7.2 to about 10.5.

2. Method according to claim 1, wherein the carbodiimide used is a compound selected from the group comprising CMC (N-cyclohexyl-N'-(2-morpholinoethyl)carbodiimide methyl-p-toluenesulfonate) and EDC (1-ethyl-3-[3-dimethylaminopropyl]carbodiimide).

3. Method according to claim 1 wherein the co-activator used is a compound selected from the group comprising s-NHS (sulfo-N-hydroxysuccinimide), HOBt (1-hydroxybenzotriazole) and N-hydroxysuccinimide.

4. Method according to claim 1 wherein the carbodiimide used is CMC (N-cyclohexyl-N'-(2-morpholinoethyl)carbodiimide methyl-p-toluenesulfonate) and the co-activator used is s-NHS (sulfo-N-hydroxysuccinimide).

5. Method according to claim 1, wherein the carbodiimide is used in an amount of 20 to 50 molar equivalents per COOH group.

6. Method according to claim 1, wherein the co-activator is used in an amount of 3 to 10 molar equivalents per COOH group.

7. Method according to claim 1, wherein the step for activation of the solid phase uses a combination of 20 to 50 molar equivalents per COOH group of CMC, in 30–200 mM phosphate buffer, in the presence of 3 to 10 molar equivalents per COOH group of sulfo-N-hydroxysuccinimide co-activator, in an acid medium with a pH ranging from about 4 to about 6.5, and in that the coupling is performed in a basic medium with a pH ranging from about 7.2 to out 10.5.

8. Method according to claim 1, wherein the step for activation of the solid phase uses a combination of 30 molar equivalents per COOH group of CMC, in 50 mM $KH_2P_4$phosphate buffer, in the presence of 5 molar equivalents per COOH group of sulfo-N-hydroxysuccinimide co-activator, at pH 6, and the coupling is performed in a medium containing one volume of a buffer of pH 8.5 and one volume of said phosphate buffer.

9. Method according to claim 1, wherein the affinity reagent contains an amine group.

10. Method according to claim 9, wherein the affinity reagent is selected from the group comprising proteins, peptides, immunoglobulins, antigens, haptens, antibodies, enzymes, enzyme substrates, oligonucleotides and polynucleotides.

11. Reactive solid complex obtained by a method according to claim 1, said reactive solid complex selected from the group consisting of solid phase/antigen complexes, solid phase/protein complexes, solid phase/peptide complexes, solid phase/hapten complexes, solid phase/antibody complexes, solid phase/immunoglobulin complexes, solid phase/oligonucleotide complexes, solid phase/polynucleotide complexes, solid phase/enzyme complexes and solid phase/enzyme substrate complexes.

* * * * *

SEQUENCE LISTING

```
<160> NUMBER OF SEQ ID NOS: 2

<210> SEQ ID NO 1
<211> LENGTH: 17
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(17)
<223> OTHER INFORMATION: Artificial sequence made for purposes of
      testing the invention.

<400> SEQUENCE: 1

Lys Gly Ser Tyr Ser Val Asp His Phe Arg Trp Gly Arg Pro Val Ser
1               5                   10                  15

Gly

<210> SEQ ID NO 2
<211> LENGTH: 7
<212> TYPE: PRT
<213> ORGANISM: Human immunodeficiency virus type 2
<220> FEATURE:
<221> NAME/KEY: PEPTIDE
<222> LOCATION: (1)..(7)
<223> OTHER INFORMATION: immunodominant epitope of gp36
```

-continued

```
<400> SEQUENCE: 2

Cys Ala Phe Arg Gln Val Cys
1               5
```